United States Patent [19]

Hevey et al.

[11] 4,387,164
[45] Jun. 7, 1983

[54] METHOD AND APPARATUS FOR CHEMICAL ANALYSIS USING REACTIVE REAGENTS DISPERSED IN SOLUBLE FILM

[75] Inventors: Richard C. Hevey, Rockport; Ronald D. Forget, Owls Head, both of Me.

[73] Assignee: FMC Corporation, Philadelphia, Pa.

[21] Appl. No.: 204,112

[22] Filed: Nov. 5, 1980

[51] Int. Cl.³ .................. G01N 33/52; G01N 33/68; G01N 33/84; G01N 35/00
[52] U.S. Cl. ............................. 436/45; 422/56; 422/72; 436/165; 436/166
[58] Field of Search .............. 422/56, 72; 436/45, 436/165, 166

[56] References Cited

U.S. PATENT DOCUMENTS

| | | |
|---|---|---|
| 3,476,515 | 11/1969 | Johnson et al. |
| 3,586,484 | 6/1971 | Anderson ............................ 436/45 |
| 3,935,303 | 1/1976 | Khromov et al. |
| 3,963,442 | 6/1976 | Bullard ............................... 436/165 |
| 3,975,162 | 8/1976 | Renn ................................. 422/56 X |
| 4,020,005 | 4/1977 | Lang ................................. 252/316 |
| 4,046,513 | 9/1977 | Johnson . |
| 4,061,468 | 12/1977 | Lange ................................. 436/166 |
| 4,062,652 | 12/1977 | Rolfo-Fontana . |
| 4,066,412 | 1/1978 | Johnson et al. . |
| 4,234,313 | 11/1980 | Faulkner ............................ 422/56 X |
| 4,234,316 | 11/1980 | Hevey ............................... 436/166 |
| 4,260,579 | 4/1981 | Barton ................................ 422/56 |

FOREIGN PATENT DOCUMENTS 750849 11/1970 Belgium .

Primary Examiner—Sidney Marantz
Attorney, Agent, or Firm—Eugene G. Horsky

[57] ABSTRACT

Automated chemical analytical method and device in which a precise measured quantity of reagent is combined with an assay medium. Prior to such delivery, the reagent, being water-soluble or dispersible, is contained within carrier solid organic binder which is fixed within and constitutes part of the device. Upon addition of an aqueous medium, the carrier binder is dissolved or dispersed, the protected precise measured quantity of reagent is concomitantly released and dissolved.

4 Claims, 4 Drawing Figures

U.S. Patent  Jun. 7, 1983  4,387,164
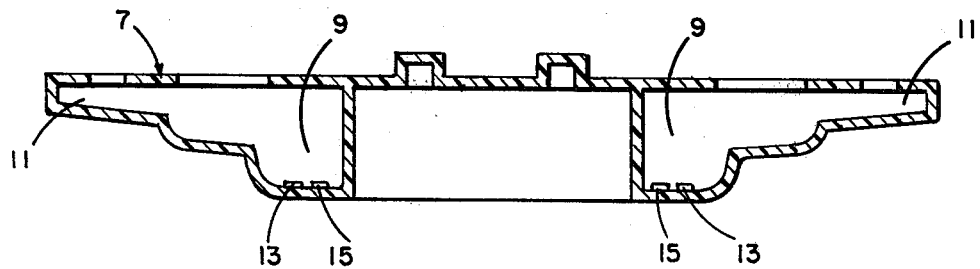
Fig. 1
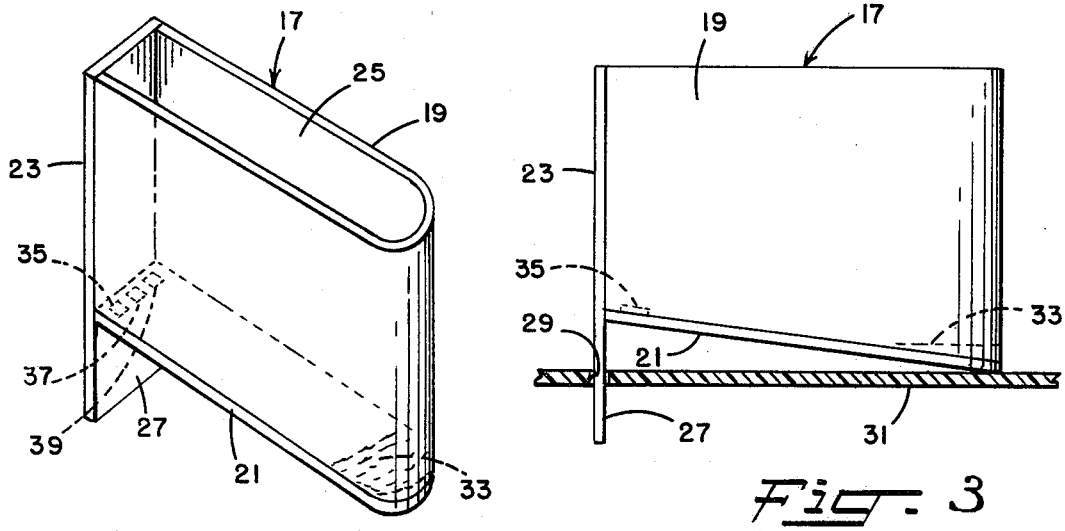
Fig. 2
Fig. 3
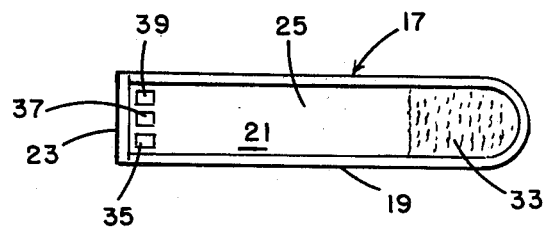
Fig. 4

METHOD AND APPARATUS FOR CHEMICAL ANALYSIS USING REACTIVE REAGENTS DISPERSED IN SOLUBLE FILM

This invention relates to chemical analyses of assay mediums, and particularly to an improved method and device for use with and which enhance automated chemical analyzers from such standpoints as functional flexibility and capacity, operation, precision and economy.

The teachings of the present invention are applicable in the analyses of a variety of assay mediums, such as, environmental, industrial and biological samples, as well as clinical specimens, such as, urine and blood serum. Solely for the sake of simplicity and ease of description, the present invention is hereafter described as employed in clinical chemistry analyses, and particularly with automated systems useful in this field.

Clinical chemistry analyses usually involve (a) sample pickup and delivery; (b) separation of proteins and analytes, as by filtration or dialysis; (c) addition and mixing of at least one reagent with the sample and, if appropriate, incubation of the mixture; (d) detection of reactions, for example, by UV (ultraviolet) or fluorometry; and (e) presentation of reaction data, such as on a strip chart, printed tape, recorder or at a computer terminal. The invention here disclosed is particularly concerned with step (c) noted above, and thus the following description is generally confined to and emphasizes the applicability of the invention in connection with such analysis step.

Analyzers presently available employ continuous flow or discrete sample analyses or centrifugation principles. Described broadly, with continuous flow analyzers, fixed volume proportions of sample and liquid or reconstituted liquid reagent are pumped into and react within and during flow through continuous tubing. The individual samples undergoing analysis and the reagents mixed therewith are separated during flow along the tubing by air bubbles. Aside from avoiding contamination of samples, it is essential that all samples be exposed to identical treatment for accurate results.

Typical of discrete sample analyzers is the "DUPONT ACA" (Automatic Clinical Analyzer) manufactured by E. I. duPont de Nemours and Company. Employed with this instrument is a disposable reagent pack which consists of a transparent plastic envelope that serves both as a reaction chamber or well and cuvette and which contains a plurality of reagent compartments each having a frangible seal which, when ruptured, facilitates the dispensing of dry or liquid reagent into the reaction envelope. In the use of this analyzer, a set volume of sample is aspirated and delivered with a diluent into the plastic envelope and, as the pack is transported, the seal of reagent compartments are ruptured and the pack is vibrated to cause the reagents to be dispensed into and mixed with the diluted sample within the plastic envelope. Reacting of reagents prior to mixing with the diluted samples and, as the packs are not reusable, the accuracy and reproducibility of results are very much dependent upon the precision with which such packs are manufactured. In the case of solid reagents, reconstitution thereof prior to reaction with the assay medium is not possible and in some analyses is desirable. Further, regardless of whether solid or liquid reagents are employed, combining of reagents with each other prior to reaction with the assay medium is likewise not possible.

Another type of discrete sample clinical chemical analyzer is commercially available from the Chemetrics Corporation and consists of a plurality of cups or wells which are removably arranged on a turntable and, when initially so arranged, have bottom portions which are inclined downwardly toward the turntable periphery. Samples to be analyzed are placed in the lower or outermost ends of the individual cups, while liquid reagents are pipetted into the higher or innermost ends of each cup at spaced locations thereof. The turntable is then automatically indexed to sequentially tilt the outermost ends of the respective cups upwardly so that the sample flows and mixes with the reagents therein, after which the reaction is aspirated into a flow cell.

Representative of centrifugal analyzers is the GEMENI TM analyzer manufactured by Electro-Nucleonics, Inc. which employs a disposable 20-place cuvette or rotor disc formed of transparent UV-transmitting plastic material. This disc consists of an outer ring containing twenty cuvettes and a concentric inner ring containing twenty wells, with the cuvettes and wells being aligned radially of the disc. After manually pipetting samples and liquid reagents into respective cuvettes and wells, the disc is placed in the analyzer. In disc loading, one cuvette contains only distilled water and another contains only a liquid reagent, while samples are pipetted in the required number of the remaining cuvettes with a standard solution pipetted in one well which is aligned radially with one of such sample-containing cuvettes. Upon rotation of the disc within the analyzer, the liquid reagents in the disc wells are propelled radially outward into the respective aligned cuvettes and mixed with the samples therein.

In general, known automated centrifugal and discrete clinical analyzers are limited in their potential to perform chemistry analyses. Such limitations can be attributed to the inability of the known anaylzers or instruments to dispense a variety of different reagents. Moreover, in preparing these known analyzers for use, reagents are reconstituted manually, after which the instruments are "primed" with liquid reagents. Once so prepared, these known instruments are capable of analyzing a batch of serum samples for a single constituent or analyte. However, single sample or stat testing and profiling require interruption of batch analyses or multiple batch runs, with one run for each test in the profile and with multiple manual liquid reagent preparation and changeovers.

Regardless of whether automated centrifugal and discrete analyzers are employed in batch or single sample testing, the problems encountered in the manual preparation and handling of liquid reagents are aggravated by the need for accurate pipetting of such liquid reagents into retaining wells, cups, or rotors of such instruments. The reagents utilized in clinical analyses are often unstable and if not used promptly, sometimes within a workday, they must be discarded. Certainly the waste of expensive reagents and the time and the potential for significant error in the manual preparation and dispensing of liquid reagents are deficiencies which must be at least minimized for the sake of efficiency and confidence in clinical chemical analyzers. Accordingly, a primary object of this invention is the provision of improved and more satisfactory method and device for conducting chemical analyses of assay mediums with automated chemical analyzers.

Another object is the provision of an improved method and device for use in automated chemical analyses which facilitate the introduction of precise measured quantities of one or more reagents into assay mediums for the quantitative determination of analytes. By this invention, the need to reconstitute reagents and the pipetting of liquid reagents, as is required with conventional automated chemical analysis systems, together with the waste of excess or unstable liquid reagents inherent in such systems, are completely avoided. Aside from facilitating chemical analyses with known instruments with greater ease, speed, and accuracy in results, the present invention enables such known analyzers to perform analyses beyond their intended capacity.

Although not limited thereto, the present invention is especially adapted for use with automatic clinical chemical analyzers which, of course, must produce precise quantitative results rapidly and accurately. As heretofore described, in methods practiced with and devices employed in known automatic discrete sample and centrifugal chemical analyzers, at least one solid or reconstituted liquid reagent is supplied to a well and subsequently and automatically the reagent and an assay medium are mixed for reaction, the reaction detected, and the reaction data presented. The term "well" as employed herein refers to a reaction area and preferably, but not necessarily, a reaction area as defined by a container or simply a depression within a surface.

By the improvement provided by the method of this invention, reagent is supplied to such one well by combining therein an aqueous medium and at least one element consisting essentially of carrier solid organic binder which is soluble or dispersible in water and which contains therein a measured quantity of water-soluble or dispersible reagent. In this manner, protected, precise measured quantity of reagent contained within the solid organic binder is released and dissolved concomitantly as the binder is dissolved or dispersed by the aqueous medium prior to or during the mixing of such reagent with the assay medium. Preferably, the measured quantity of reagent is dispersed throughout the carrier solid organic binder and may be dissolved completely within the aqueous medium prior to mixing with the assay medium.

As employed herein, "reagents" are chemically active materials which, when released from the carrier solid organic binder, combine with each other and/or one or more constituents of an assay medium to provide an intermediate or final product having chemical characteristics different from the reagents and/or assay medium prior to the combining thereof. For example, reagents may react only with the analyte to be determined when such reagent is combined with the assay medium, while still other reagents, when dissolved or dispersed in an aqueous medium may react to provide a solution having a pH, salt concentration, or buffering capacity necessary for reacting with one or more constituents of an assay medium.

By the method of this invention, aqueous medium in such one well may be combined with a plurality of elements, each of which consists essentially of carrier solid organic binder which is soluble or dispersible in water and having dispersed therein a precise measured quantity of reagent. The reagent in one or more of such elements may be reactive with one or more reagents in other of such elements. If desired, prior to any mixing with the assay medium, the carrier binder of all such elements are completely dissolved or dispersed by the aqueous medium so that the reagents therein are partially or completely dissolved, mixed with each other and reacted before reacting with the assay medium.

As an alternative to employing a plurality of elements having characteristics as described above, a single element may be employed which consists of carrier organic solid binder which is soluble or dispersible in water and has dispersed therein a precise measured quantity of each of a plurality of water-soluble or dispersible reagents. In such alternative system, reagents which are reactive with each other may be dispersed within separate areas of the element.

A still further alternative is a single element consisting of layers of carrier solid organic binder which is soluble or dispersible in water and having dispersed in each such layer a precise measured quantity of at least one water-soluble or dispersible reagent. In such element, adjacent contacting layers of carrier binder containing reagents which are reactive with each other are separated by a layer of water-soluble binder free of reagents or by a layer of inert water impervious material.

The improved device of this invention may consist of a cup as employed in the Chemetrics ® discrete sample analyzer heretofore described, or a segmented disc or rotor, such as used with the GEMENI ™ centrifugal analyzer as heretofore described herein, each of which includes a well having fixed therein, at a position to be contacted by aqueous medium supplied thereto, an element consisting essentially of carrier solid organic binder which is soluble or dispersible in water and which contains a precise measured quantity of water-soluble or dispersible reagent. The described element may be in the form of a preformed film fixed to the well of the device by adhesion or fixed as a film formed by casting the carrier binder, containing the reagent, in a flowable condition and then setting the same. It will be apparent that the improved device of the present invention can be readily transported and stored, that the precise measured quantities of reagents contained within the carrier binder of the element are protected and thus remain in stable form, and that only an aqueous medium need be added to the well of the device containing such element to provide the proper reagent concentration for the analysis to be performed.

The binders which can be used in the present invention include various polymeric materials such as dextran, water-soluble polyacrylamide, polyacrylic acid and water-soluble metal salts thereof, water-soluble polyvinyl alcohol, polyethylene glycol, polyethylene oxide, polyvinylpyrrolidone, clarified guar gum, water-soluble carboxymethyl cellulose, water-soluble hydroxyethyl cellulose, water-soluble methyl cellulose, algin, carrageenan, xanthan gum, starch, water-soluble copolymers of maleic anhydride with various vinyl monomers as described, for example, in U.S. Pat. No. 2,047,398 particularly copolymers of maleic anhydride with vinyl ether, or vinyl ester, or their corresponding salts. There can also be present along with the binder, conventional humectants or surface active agents (dispersing agents) to maintain the flexibility of the binder and to facilitate or accelerate its dispersion or dissolution in water. In addition, binders of non-polymeric, relatively low molecular weight molecules can be used including sorbitol, potassium sodium tartrate, mannose, and sucrose. Binders composed of mixtures of two or more different materials can be used.

The reagents which can be incorporated in the binder can be any of the water-soluble or water-dispersible materials which are commonly employed in analytical procedures, such as enzymes, enzyme substrates, antibodies, antigens, haptens, inorganic and organic reagents, buffers, salts, and the like, as well as radioactively tagged or fluorescent reagents of the foregoing types including nonisotopic tags such as enzymes, cofactors, luminescent agents, and the like.

The element containing binder and reagent may be of any desired thickness, but is preferably from 0.01 to 2 mm. thick for ease in handling when it is prepared separate from a well to which it is subsequently applied.

The relative proportions of reagent and of water-soluble polymeric binder in the device can be varied widely depending upon the size or amount of the measured quantity which is desired and is a matter of convenience. Usually it is most convenient to employ a device in which the water-soluble binder amounts to about 2 to 95% by weight of the element while the reagent constitutes the remainder. While there may be included in a single element two or more reagents which are compatible, i.e., nonreactive, with each other, those which are reactive (i.e., which react with each other or which cause decomposition of one or the other over a period of time) must be present only in separate areas of an element or in discrete and separate elements.

The reagents can be incorporated in the element binder in a variety of ways. The reagent can be mixed with the binder while the latter is in a molten form or in the form of a solution in a volatile solvent, after which the mixture is formed into a film of the desired thickness separate from or within a well of the device and allowed to dry or cool in order to solidify it. The element of water-soluble binder can also be formed separately, from a solution of the binder or from a melt, also separate from or within a well of the device, after which a solution or dispersion of the reagent in a suitable liquid vehicle can be applied to the surface of the element, allowed to diffuse into the element and the film dried. In some cases, the reagent in dry, finely-divided particulate form can be spread on the surface of the binder element while it is still tacky or adhesive and then subsequently solidified, or onto a solidified binder element after which the latter is melted and resolidified. While forced air drying can usually be employed in forming the film and/or incorporating the reagent in the film, vacuum or freeze-drying can also be employed in the case of heat-sensitive materials.

The device of the present invention is employed to accurately deliver precise quantitative amounts of reagents in analytical procedures, especially procedures requiring reagents which when mixed together react with each other or become unstable and lose their potency over a period of time. Of particular importance, and as heretofore mentioned, is that the present invention can be adapted for use in carrying out a wide variety of chemical analyses, not only in the field of clinical chemistry, but in chemical research, water analysis, and chemical process control. The invention is well suited for use in chemical testing of body fluids such as blood, serum, and urine, since in this work a large number of repetitive tests are frequently conducted and these results are needed within a short time after the sample is taken. The device, for example, can be adapted for use in carrying out quantitative analyses for many of the blood components which are routinely measured. Thus the device can be adapted for use in the analyses of such blood components as albumin, bilirubin, area nitrogen, serum glutamicoxalacetic transaminase, chloride, total protein, glucose, uric acid, acid phosphatase and alkaline phosphatase.

In the drawing,

FIG. 1 is a vertical section taken diametrically through one embodiment of the improved device of the present invention;

FIG. 2 is a perspective view of another embodiment of the improved device of the present invention;

FIG. 3 is a side view of the device shown in FIG. 2; and

FIG. 4 is a plan view of the device shown in FIGS. 2 and 3.

The device shown in FIG. 1 includes a conventional rotor or head 7 as employed with known automatic centrifugal chemical analyzers, such as the GEMENI TM analyzer heretofore described, that includes a series of separated wells 9 for containing reagent and a like number of sample wells 11, each being aligned radially with an individual reagent well 9. In accordance with the teachings of the present invention, fixed within the reagent wells 9 are one or more elements, such as indicated at 13 and 15, each of which consists essentially of carrier solid organic binder which is soluble or dispersible in water and having dispersed therein a precise measured quantity of water-soluble or dispersible reagent. In the illustrated embodiment different reagents are dispersed within the carrier binder of the elements 13 and 15, and, if the reagents in such elements are reactive with each other, there is no risk of such reaction in view of the physical separation of these elements 13 and 15.

Employing the improved device shown in FIG. 1, with known automatic centrifugal clinical chemical analyzers enables simplified profile chemistry analyses to be obtained. In the use of the device or rotor show in FIG. 1, with the reagent wells 9 having fixed therein the appropriate reagent elements 13 and 15, a technician need only add an appropriate amount of water to each of such cells 9 to dissolve or disperse the carrier binder of such elements, releasing and dissolving the reagents therein and thus providing a reconstituted combined reagent of precise concentration. Samples or assay mediums are then pipetted into the respective sample wells 11, after which the device is placed in the known automatic centrifugal clinical chemical analyzer which functions in its ordinary manner to rotate the device, causing the reagents to flow radially from the wells 9 and into the wells 11 so as to mix and react with the samples or assay mediums therein. Such known analyzers will then automatically detect the reaction and present the reaction data.

Illustrated in FIGS. 2-4 is one of a series of cups such as employed in the automatic clinical chemical analyzer made available by the Chemetrics Corporation, as heretofore mentioned. The cup or device 17 includes a side wall 19, an included bottom wall 21 and rear wall 23, all of which are formed of plastic material and together define a well 25. A support leg 27 is formed as an extension of the rear wall 23 for insertion into one of a series of slots 29 in a tray 31, a portion of which is shown in FIG. 3, and is carried by a turntable not shown, that is part of the known automatic analyzer.

In the conventional use of such the automatic analyzer, a series of such cups or devices 17 are placed on the tray 31 with the legs 27 thereof inserted into the tray slots 29. When the cups 17 are so positioned on the tray 31, the wells 25 therein are deepest at the free end portions thereof in view of the inclined bottom walls 21 of such cups 17. As shown in FIG. 2, the assay medium or sample, indicated at 33, is pipetted into the deeper end of the well, while one or more liquid reagents, not shown, are pipetted into the shallow end thereof. The tray 31 is then inserted into the automatic analyzer which is equipped to tilt the respective cups 17 so as to raise the free ends and cause the assay medium to flow, mix, and react with the liquid reagents.

In lieu of pipetting liquid reagents into the cup wells 25, and in accordance with the present invention, elements 35, 37 and 39 are fixed to the bottom well of a cup 17, each such element consisting essentially of carrier solid organic binder which is soluble or dispersible in water within which is dispersed a precise measured quantity of at least one water-soluble or dispersible reagent. Reagents which react with each other may well be placed in the separated elements 35, 37, and 39. The tray 31 is then placed in the automatic analyzer which performs its intended function. It will be apparent that with the device of the present invention, premature mixing of reagents with each other, as when transporting the tray 31 to the analyzer, is not possible.

The following specific examples are intended to illustrate the nature of the invention without acting as a limitation upon its scope.

EXAMPLE I—ANALYSES FOR INORGANIC PHOSPHATE

Using a rotor of a GEMENI TM centrifugal analyzer, the device of the present invention was prepared as follows:

1. The inside surface of such rotor was made hydrophilic by plasma treatment.

2. Reagent elements were prepared by mixing into water-soluble polyethylene glycol 1500 and polyvinylpyrrolidone (MW=10,000), as follows:

A. Color Reagent: A mixture of ammonium molybdate (100 mg) and sodium bisulfate monohydrate (340 mg) was prepared in a 5 ml solution of 0.001% polyethylene glycol 1500. 15 $\mu$l of the mixture was then dried down as a film in each of the inside well (cavities) of the transfer disc, except well No. 1, which is used as a water blank.

B. Reductant: Reductant mixture was prepared by weighing out 100 mg of ascorbic acid and 500 mg SDS (lauryl sulfate) in a 5 ml solution of 0.001% polyvinylpyrrolidone. 15 $\mu$l of this mixture was dried down as a film in each of the outer well (cavities) of the transfer disc, except well No. 1.

The procedure then practiced was as follows: Dispersed 15 $\mu$l of water, phosphate standard, quality control sera and patient sample into outer wells 1 to 4. Added 0.700 ml of distilled water to all the inner wells of the disc (the inner wells containing the reagents). Mixed and dissolved the reagents by gentle rocking. Loaded the device of this invention onto the analyzer which was appropriately programmed for inorganic phosphate determination.

Results obtained were as follows: Standards (aqueous), quality control sera (normal and abnormal), patient's sera were evaluated using the device of this invention. The results of the analysis gave the expected values comparable to the manual ammonium molybdate procedures described in the literature. The precision for both procedures was similar to that obtained by others and ourselves.

EXAMPLE II—ANALYSIS OF ALBUMIN

A rotor of a centrifugal analyzer was prepared as in Example I using polyethylene glycol 4000 and reagents, as follows:

A. Buffer: Weighed out 7.136 g citric acid monohydrate, 3.017 g potassium hydroxide pellets and 0.340 g PEG-4000 and dissolved in sufficient quantity of water to make a total volume of 50 ml. 50 $\mu$l of this solution was dried down as a film in the outside wells of the device, except for well No. 1.

B. Dye: Prepared a 50 ml mixture containing 4.104 g Brij ® 35 (30% solution W/V), 0.1047 g bromocresol green, 1.771 g PEG-4000, 0.0625 ml 10 N NaOH solution, and sufficient distilled water. 25 $\mu$l of this solution was dried down as a film in the inside wells of the device, except well No. 1.

Automated Procedure: The device was loaded as follows: Pipetted 0.010 ml of water in outside wells Nos. 1 and 2, and pipetted 0.010 ml of 4 g/100 ml albumin standard to outside well No. 3 and 0.010 ml quality controls and patient serum samples in outside well No. 4 onwards. Added 1 ml of distilled water to all of the inside wells (containing dye reagent) and rocked gently to dissolve the dye. Loaded the transfer disc into the analyzer, which was programmed for albumin determinations.

Results obtained were as follows: The data obtained with the above system were analyzed for accuracy and precision using quality control sera and patient samples. The result of the analyses show that both the manual procedure for albumin and the present procedure using dried reagents yield comparable values for the samples.

EXAMPLE III—ANALYSES FOR CREATININE

A rotor of a centrifugal analyzer was prepared as in Example I using sorbitol and reagents, as follows:

A. Alkaline reagent: Weigh out 10 grams sodium hydroxide, 8.7 grams of sodium potassium tartrate and 8.7 grams of sorbitol and dissolve in water to a final volume of 100 ml.

B. SDS reagent: Dissolve 10 grams of sodium dodecylsulfate in 80 ml of water and dilute to a volume of 100 ml.

C. Picrate reagent: A solution containing 3.05 grams picric acid and 5.00 grams sorbitol was adjusted to a pH of 2.0 with lithium hydroxide and diluted to a final volume of 100 ml with water.

35 $\mu$l of the alkaline reagent was added to the inside wells (cavities) of a transfer disc except for well No. 1. The reagent was then dried for 16 hours at 50° C. in a drying oven. 5 $\mu$l of SDS reagent and 35 $\mu$l of picrate reagent were then similarly applied to the well but in adjacent spots to the dried sodium hydroxide. The reagents were dried for 2 hours at 50° C.

Automated procedure: The device was loaded as follows: Pipetted 700 $\mu$l of water in outside wells Nos. 1 and 2, and pipetted 60 $\mu$l of creatinine standard to outside well No. 3 and 60 $\mu$l of quality controls and patient sample in outside well No. 4 onwards. Added 700 $\mu$l of distilled water to all of the inside wells containing the three reagent films, and rocked gently to dissolve the reagents. Loaded the transfer disc into the analyzer, which was programmed for creatinine determinations.

Results obtained were as follows: The data obtained with the above system showed that both the manual procedure for creatinine and the present procedure using dried reagents yield comparable values for the samples and quality control sera.

We claim:

1. In a method of chemically analyzing an assay medium in which at least one solid or liquid reagent is supplied to a well and subsequently and automatically the reagent and an assay medium are mixed for reaction, the reaction detected, and the reaction data presented, the improvement comprising supplying reagents to such one well by combining therein an aqueous medium and at least one element consisting essentially of carrier solid organic binder which is soluble or dispersible in water and in which is dispersed at separate locations thereof a precise, measured quantity of each of at least two water-soluble or dispersible reagents which are reactive with each other whereby the protected, measured quantities of reagents dispersed within the solid organic binder are completely dissolved or dispersed concomitantly as the binder is dissolved or dispersed by the aqueous medium, mixed with each other, and reacted prior to mixing with the assay medium.

2. In a device for use with an apparatus for automatically chemically analyzing an assay medium, said device having a well into which is supplied at least one solid or liquid reagent which, when said device is used with an analyzing apparatus, is automatically mixed with an assay medium for reaction, the reaction detected, and the reaction data presented, the improvement comprising an element fixed within the well of said device in position to be contacted by an aqueous medium to be supplied thereto, said element consisting essentially of carrier solid organic binder which is soluble or dispersible in water and which contains therein at separate locations thereof a measured quantity of each of at least two water-soluble or dispersible reagents which are reactive with each other whereby the protected and unreacted reagents are completely dissolved or dispersed and react with each other concomitantly as the carrier binder is dissolved or dispersed upon supplying aqueous medium into the well of such device.

3. In a device as defined in claim 2 wherein said element is in the form of a solid film fixed within the well of said device by adhesion.

4. In a device as defined in claim 3 wherein said element is in the form of a solid film and is adhered within the well of said device by being cast therein a flowable condition and solidifying the same.

* * * * *

UNITED STATES PATENT AND TRADEMARK OFFICE
CERTIFICATE OF CORRECTION

PATENT NO. : 4,387,164
DATED : June 7, 1983
INVENTOR(S) : Richard C. Hevey and Ronald D. Forget It is certified that error appears in the above-identified patent and that said Letters Patent is hereby corrected as shown below:

Column 5, line 67, "area nitrogen" should read -- urea nitrogen --.

Signed and Sealed this

Twenty-fifth Day of October 1983

[SEAL]

Attest:

GERALD J. MOSSINGHOFF

Attesting Officer　　Commissioner of Patents and Trademarks